United States Patent [19] [11] 4,291,230
Heiss [45] Sep. 22, 1981

[54] FLUOROMETRIC ANALYZER INCLUDING SHUTTER MEANS FOR SIMULTANEOUSLY SHIELDING SAMPLE AND PHOTODETECTOR DURING SAMPLE CHANGE

[75] Inventor: Louis R. Heiss, Annapolis, Md.

[73] Assignee: Baxter Travenol Laboratories, Inc., Deerfield, Ill.

[21] Appl. No.: 18,152

[22] Filed: Mar. 7, 1979

[51] Int. Cl.³ ................ G01N 21/38; G01J 1/58; G01N 21/01
[52] U.S. Cl. ..................... 250/458; 250/461 R; 356/244
[58] Field of Search ............ 250/458, 461 R, 576, 250/461 B, 373; 356/440, 244; 250/459

[56] References Cited

U.S. PATENT DOCUMENTS

| | | | |
|---|---|---|---|
| 3,610,927 | 10/1971 | Hausser | 250/328 |
| 3,764,214 | 10/1973 | Heiss | 356/440 |
| 3,917,404 | 11/1975 | Heiss | 250/576 |
| 4,099,920 | 7/1978 | Heiss | 356/244 |
| 4,213,703 | 7/1980 | Haunold et al. | 356/244 |

FOREIGN PATENT DOCUMENTS 560489 9/1978 U.S.S.R. .............. 250/328

OTHER PUBLICATIONS

Strehler, "Adenasine-5'-triphosphate and Creatine Phosphate Determination with Luciferase", *Methods of Enzymatic Analysis,* Bergmeyer (editor), Academic Press, 1963, pp. 559-563.

*Primary Examiner*—Alfred E. Smith
*Assistant Examiner*—Carolyn E. Fields
*Attorney, Agent, or Firm*—Robert A. Benziger; Eugene M. Cummings; Paul C. Flattery

[57] ABSTRACT

A fluorometric analyzer includes a head assembly wherein the photomultiplier tube and excitation lamp of the analyzer are received in respective cavities and a transparent test cell is provided to receive a liquid sample. A first optical passage is provided between the lamp cavity and the test cell, and a second optical passage at right angles to the first optical passage is provided between the test cell and the photomultiplier tube cavity. A manually rotatable shutter assembly concentrically disposed about the test cell includes apertures for allowing light to pass through the optical passages when the shutter is rotated to a first position, and for simultaneously blocking the passage of light through the passageways when the shutter is rotated to a second position. Rotation of the shutter is limited by a first guide pin, and a second guide pin provides a desired degree of friction between the shutter assembly and the head assembly housing.

7 Claims, 14 Drawing Figures

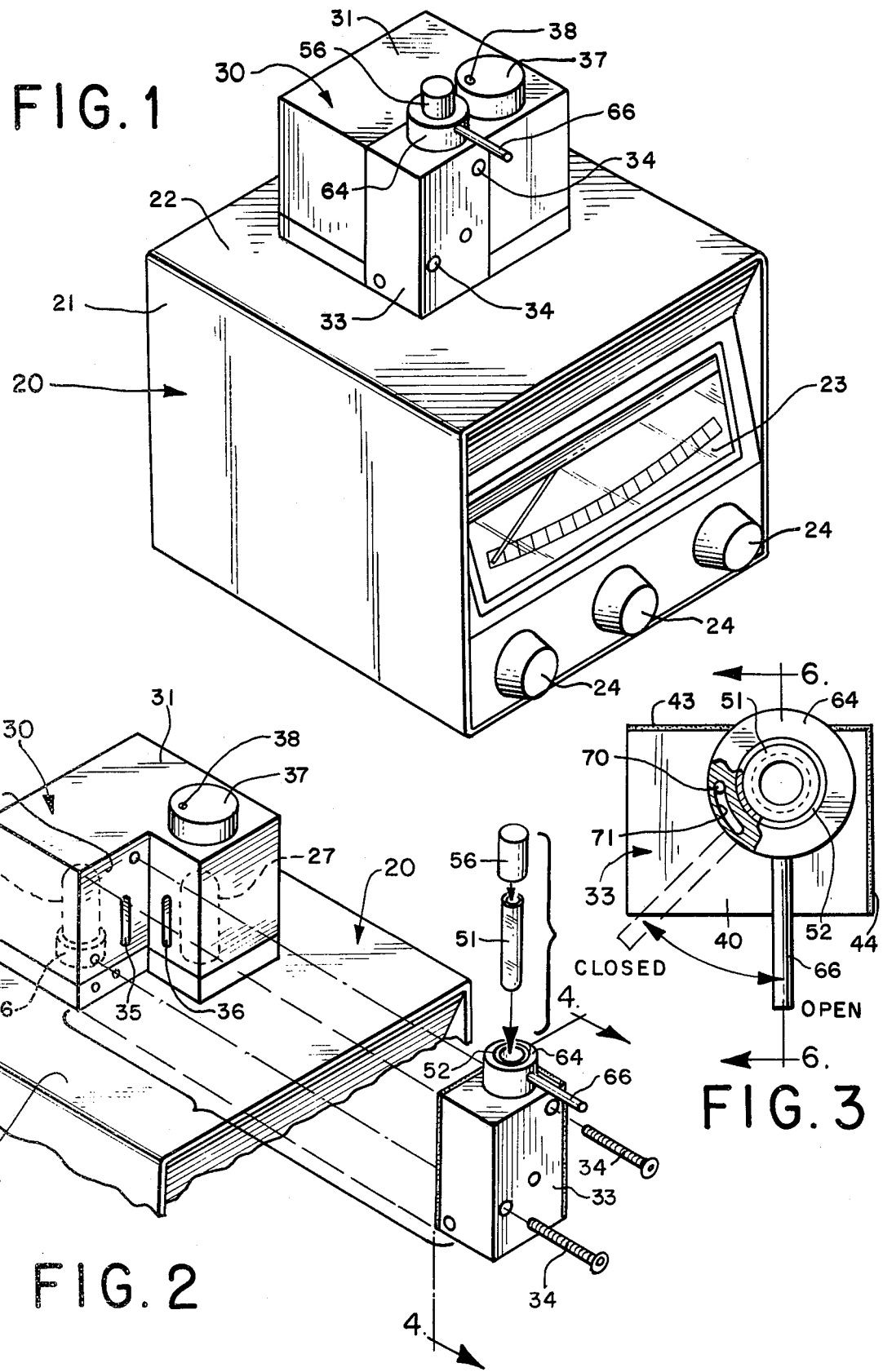

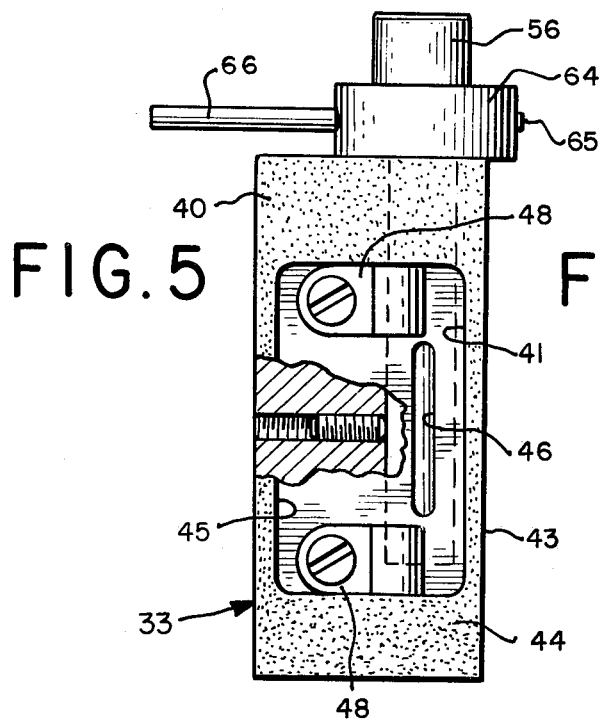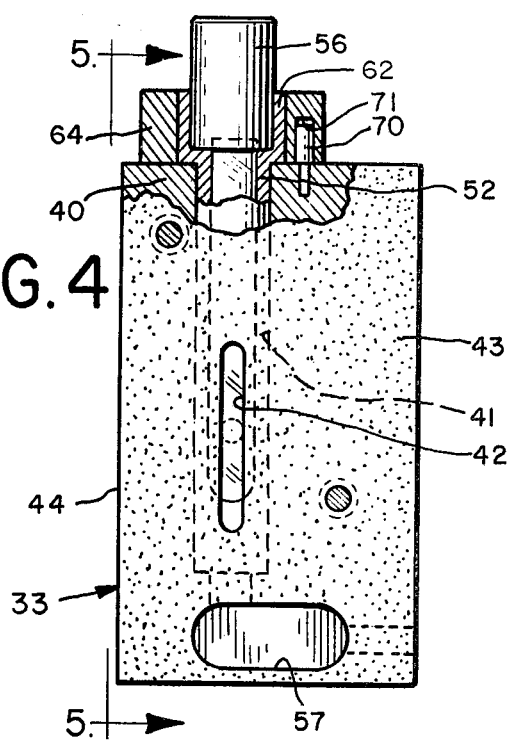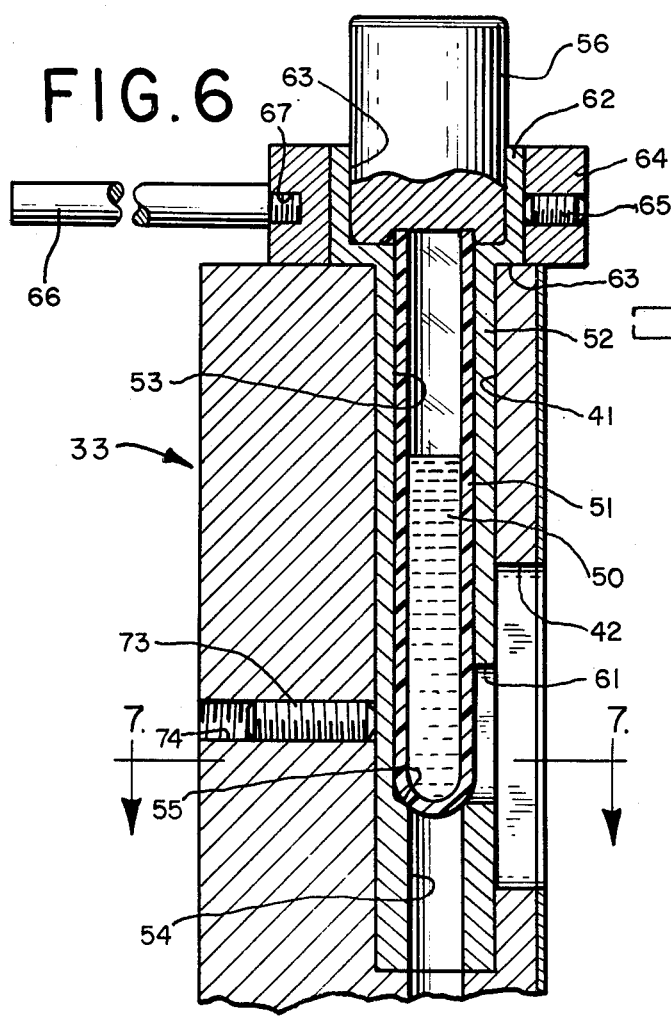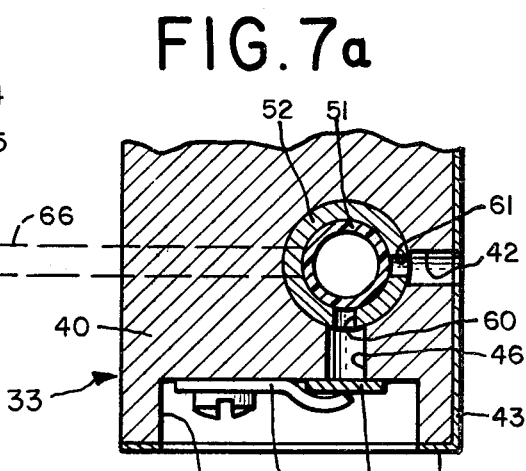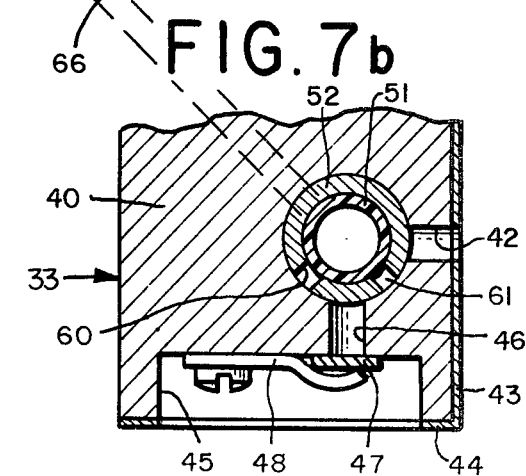

U.S. Patent  Sep. 22, 1981  Sheet 3 of 3  4,291,230
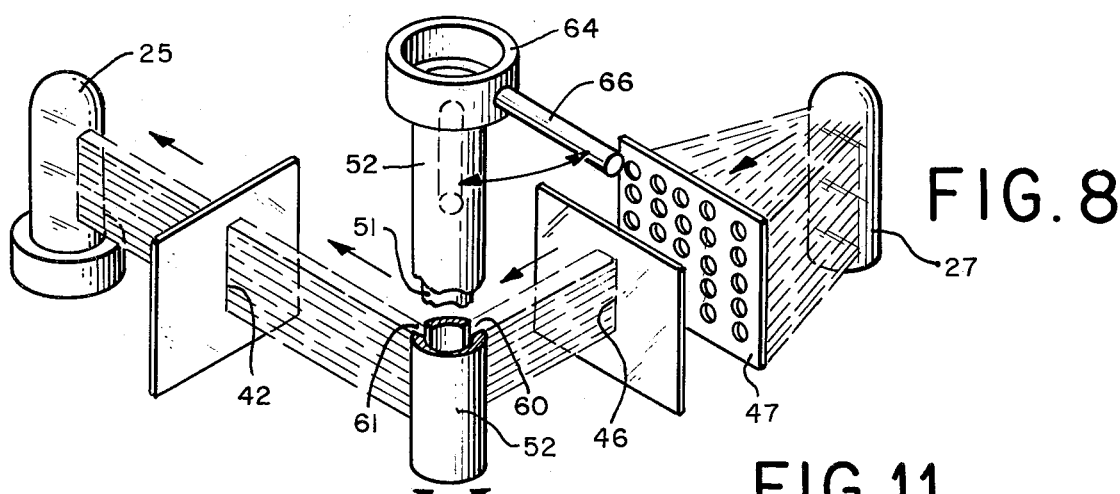
FIG. 8
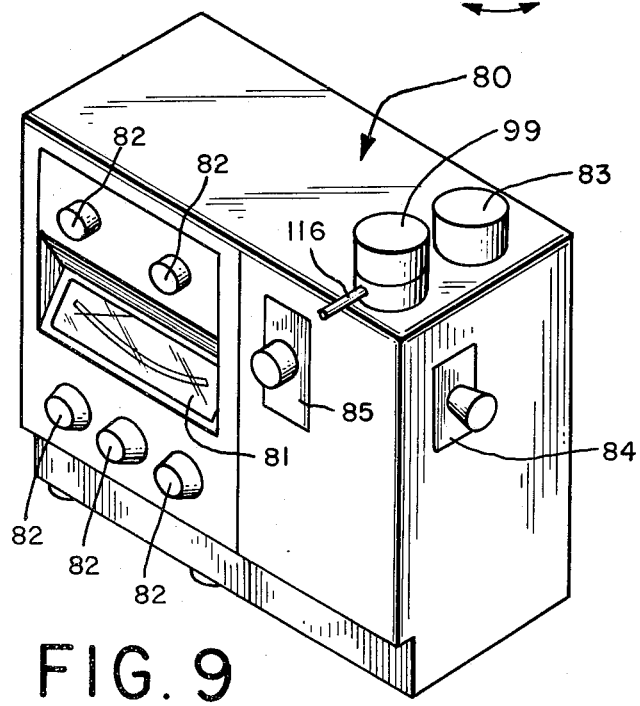
FIG. 9
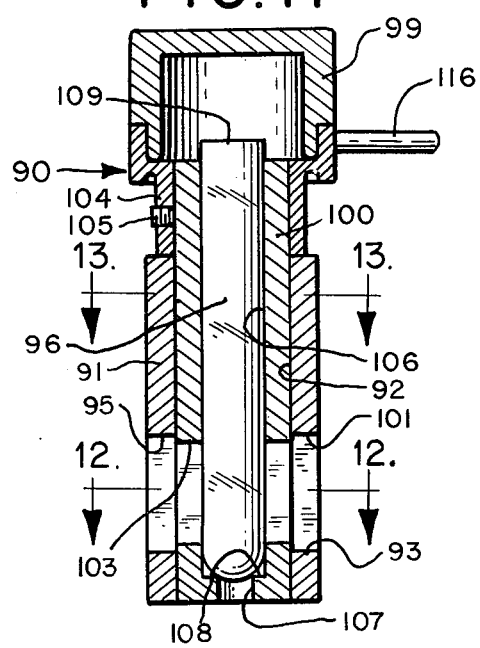
FIG. 11
FIG. 12
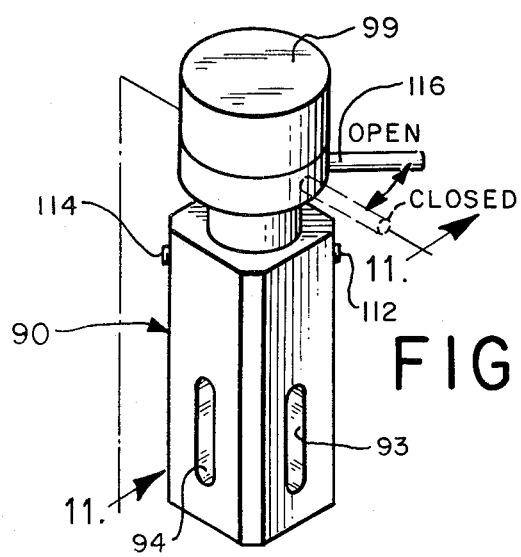
FIG. 10
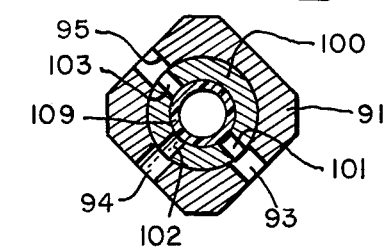
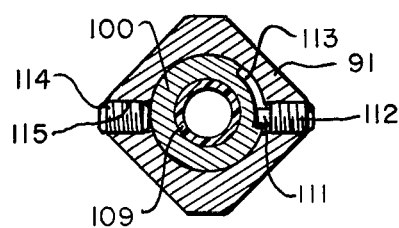
FIG. 13

FLUOROMETRIC ANALYZER INCLUDING SHUTTER MEANS FOR SIMULTANEOUSLY SHIELDING SAMPLE AND PHOTODETECTOR DURING SAMPLE CHANGE

BACKGROUND OF THE INVENTION

The present invention is directed generally to fluorometric analyzers, and more particularly to an improved head assembly for a fluorometer wherein the photomultiplier tube of the analyzer is protected against exposure to incident and reflected ambient light.

Fluorometric analyzers such as the Fluoro-Monitor and Fluoro-Colorimeter (Trademarks) manufactured by the American Instrument Company Division of Baxter Travenol Laboratories, Inc. find wide application in detecting fluorescence in liquid samples. In these instruments the samples are exposed through an appropriate filter to radiation from an excitation lamp light source, and fluorescence within the sample is detected by a detector in the form of a photomultiplier tube disposed at right angles to the direction of excitation. In the Fluoro-Monitor analyzer, the excitation lamp, test cell, photomultiplier tube and filter are incorporated in a compact head assembly which provides for the shortest possible optical paths between the light source, sample and detector for optimum analyzer sensitivity. This head assembly is described in U.S. Pat. No. 3,917,404, which issued to the present inventor on Nov. 4, 1975 and is assigned to the present assignee.

In fluorometric analyzer head assemblies the liquid sample being analyzed may be contained in either a closed-end cuvette, wherein a specific quantity of liquid is observed, or in an open-ended flow cell, wherein a continuous flow of liquid is observed. Where individual cuvettes are being analyzed, the possibility exists of the sensitive photomultiplier tube being exposed to ambient light, either directly or as a result of reflections when the cuvettes are being changed. Where a flow-cell is being utilized, the possibility for such exposure also exists while changing or adjusting the flow cell, or when it becomes necessary to correct a leaking connection with associated tubing. Exposure of the sensitive photomultiplier tube to the relatively strong incident or reflected light has the effect of reducing the photomultiplier tube sensitivity for a period of time, making subsequent measurements inaccurate and requiring the operator to wait for the detector to restabilize before proceeding with a measurement.

Prior-art fluorometric analyzer head assemblies, such as that of the aforementioned Fluoro-Monitor analyzer, incorporated a shutter for the excitation lamp which could be conditioned to block light rays from reaching the sample. While effective for this purpose, the shutter did not prevent ambient light from reaching the photomultiplier tube upon removal of the test cell. In bioluminescence applications wherein no excitation light source is utilized, such as those described in Bergmeyer, *Methods of Enzymatic Analysis,* Academic Press, 1963, pages 559-563, it has been proposed to provide a rotatable shutter having a single slot-shaped aperture over a cuvette to control the incidence of light on an associated photomultiplier tube. This arrangement is applicable to bioluminescence and chemiluminescence applications only, since it does not provide for simultaneously controlling the light from the excitation lamp required for exciting the sample to fluorescence in fluorometric applications.

Accordingly, it is a general object of the present invention to provide a new and improved fluorometric analyzer wherein samples may be changed without exposing the light detector thereof to incident or reflected light.

It is a more specific object of the present invention to provide a new and improved head assembly for a fluorometric analyzer wherein a sample may be conveniently changed or adjusted without exposing the light detector of the analyzer to incident or reflected radiation.

SUMMARY OF THE INVENTION

The invention is directed to a fluorometric analyzer, and head assembly therefore, for measuring fluorescence in a liquid sample contained within a test cell of generally cylindrical proportions. The analyzer and head assembly comprise means including an excitation lamp for applying radiation to the sample, means including a photodetector for detecting light produced as a result of fluorescence in the sample, and a housing defining respective chambers for receiving the photodetector and the excitation lamp, and an additional chamber for receiving the test cell, and further defining optical passageways between the excitation lamp and the test cell, and between the test cell and the photodetector, the optical passageways being arranged at generally right angles. In accordance with the invention, shutter means including a sleeve disposed within the housing concentrically with the test cell are provided for simultaneously controlling the passage of light through the first and second optical passageways, the sleeve being mounted for rotation between first and second positions and including first and second apertures arranged about the circumference thereof for admitting light through said first and second optical passageways when the sleeve is in the first position, and for blocking light through the first and second optical passageways when the sleeve is in the second position.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

FIG. 1 is a perspective view of a fluorometric analyzer including a fluorometer head assembly constructed in accordance with the invention.

FIG. 2 is a perspective view of the analyzer head assembly showing the test cell module and cuvette sample holder thereof in a detached state.

FIG. 3 is an enlarged plan view of the test cell module partially broken away to illustrate the shutter assembly incorporated therein.

FIG. 4 is an enlarged rear elevational view of the test cell module partially in cross-section to show details of the shutter assembly.

FIG. 5 is an enlarged side elevational view of the test cell module partially in cross-section to show additional details of the shutter assembly.

FIG. 6 is an enlarged cross-sectional view taken along line 6—6 of FIG. 3 showing the test cell and shutter assembly as incorporated in the test cell module.

FIG. 7a is an enlarged cross-sectional view taken along line 7—7 of FIG. 6 showing the shutter assembly in an open or operative position.

FIG. 7b is an enlarged cross-sectional view similar to FIG. 7a showing the shutter assembly in a closed or non-operative position.

FIG. 8 is an expanded diagramatic view of the principal components of the fluorometric analyzer useful in understanding the operation of the shutter assembly.

FIG. 9 is a perspective view of a fluorometric analyzer incorporating an alternate embodiment of the invention.

FIG. 10 is an enlarged perspective view of the test cell module utilized in the fluorometric analyzer of FIG. 9.

FIG. 11 is an enlarged cross-sectional view of the test cell module taken along line 11—11 of FIG. 10 showing the shutter assembly incorporated therein.

FIG. 12 is a cross-sectional view taken along line 12—12 of FIG. 11 showing certain details of the shutter assembly.

FIG. 13 is a cross-sectional view taken along line 13—13 of FIG. 11 showing additional details of the shutter assembly.

DESCRIPTION OF THE PREFERRED EMBODIMENT

Referring to the drawings, and particularly to FIG. 1, a fluorometric analyzer 20 is shown which includes a main housing 21 provided with vertical sidewalls and a horizontal top wall 22. The analyzer includes a readout meter 23 and conventional operating controls 24 on the front panel of housing 21, and may employ conventional circuitry to provide meter indications indicative of fluorescence in a sample liquid in a manner well known to the art. To measure fluorescent light emitted from a sample, the analyzer includes a photosensitive detector element in the form of a photomultiplier tube 25 (FIG. 2) mounted in a socket 26 so as to project upwardly through an aperture formed in top wall 22. To provide a source of excitation for the sample, the analyzer includes an excitation lamp 27 (FIG. 2) which projects upwardly from top wall 22 in parallel-spaced relationship to photomultiplier tube 25. The lamp may at times be removed to enable the base portion of the photometric analyzer 20 to be employed with an alternate form of head assembly (not shown) having a reaction chamber wherein bioluminescence or chemiluminescence tests may be performed, as described in U.S. Pat. No. 3,764,214, which issued to the present inventor on Oct. 9, 1973, and is assigned to the present assignee.

Designated generally 30 is a head assembly which may be employed in cooperation with the base portion of analyzer 20 to perform fluorometric analysis of liquid samples. This head assembly, which is described in the previously identified U.S. Pat. No. 3,917,404, comprises a main block assembly consisting of a generally L-shaped base assembly 31 defining a corner recess 32. A generally rectangular test cell module 33 is secured in recess 32 in close-fitting contact with base assembly 31 by means of a pair of diagonally opposed clamping screws 34. Slot-shaped apertures 35 and 36 on the base module 31 define respective passageways through which light communication is established between the test cell module 33, and photomultiplier tube 25 and excitation lamp 27, when test cell module 33 is seated in recess 32. A cylindrical shutter sleeve assembly including a projecting opaque cover cap 37 may be arranged coaxially with excitation lamp 27 on base module 31 to enable the light emission from lamp 27 to be selectively controlled by the operator. This shutter sleeve is rotatably mounted in base module 31 by conventional means and includes a vertical slot which is registerable with aperture 36. As shown in FIGS. 1 and 2, the shutter sleeve projects upwardly a short distance from the top surface of base module 31 and includes an opaque cover cap 37 secured on its top portion, this cover cap being provided near its periphery with a small transparent index window 38 in the same radial vertical plane as the shutter sleeve slot so that in one position thereof the shutter sleeve may be aligned to place the slot in registration with window 36. By rotating the shutter sleeve away from this position by means of cover cap 37 window 36 may be blocked, enabling dark current measurements to be made with the photometric analyzer.

Referring to FIGS. 3-5, the flow cell module 33 consists of a generally rectangular block 40 having a cylindrical vertical bore or recess 41. A first vertical radial slot 42 extends from recess 41 perpendicularly to the rear face 43 of module 33. The right face 44 of module 33, as viewed in FIGS. 2 and 3, is formed with a rectangular filter-receiving recess 45 and with a vertical slot 46 extending radially from recess 41 and at right angles to slot 42, thereby communicating perpendicularly with filter recess 45. A suitable excitation filter plate 47 may be removably secured in recess 45 by means of spring clips 48 in a manner well known to the art. When test cell module 33 is seated in recess 32 slots 42 and 46 come into registration with slots 35 and 36, respectively, thereby providing unobstructed light paths between excitation lamp 27 and the interior of recess 41, and between photomultiplier tube 25 and the interior of recess 41, respectively.

Referring to FIG. 6, a quantity of a liquid 50 to be analyzed is contained within the interior of bore-shaped recess 41 by means of a conventional transparent test cell or cuvette 51. The cuvette, which is transparent and generally test-tube shaped, is seated within an opaque cylindrical metal sleeve 52 slidably received within bore 41. To provide for stable positioning of cuvette 51, the interior bore of sleeve 52 preferably includes a first or upper portion 53 of a diameter substantially corresponding to the outside diameter of the cuvette, and a second or lower portion 54 of somewhat reduced diameter providing an annular shoulder 55 against which the bottom closed end of the cuvette rests. Where continuous flow measurements are required, the cuvette can be replaced by a cylindrical transparent flow tube (not shown) extending through both portions of the sleeve interior. This flow tube is connected to an external flow system at its top end by removal of a cap 56 otherwise provided to cover the open end of cuvette 51, and to the external flow system at its bottom end by appropriate tubing means through a transverse access aperture 57 (FIG. 4). Reference is made to the afore-identified U.S. Pat. No. 3,917,404 for further detail on the installation of a flow tube in the test cell module.

To enable light from excitation lamp 27 to fall on the test liquid 50 shutter sleeve 52 is provided with a first slot-shaped aperture 60 positioned for registration with slot 42. Similarly, to provide an optical path to photomultiplier tube 25 where light emitted as a result of fluorescence in the test sample, sleeve assembly 52 is provided with a second slot-shaped aperture 61 in substantial registration with slot 42 (FIG. 7a). Aligned as shown in FIG. 7a, these slots allow the unobstructed passage of light along the perpendicularly-aligned passageways defined by apertures 36 and 46, and apertures 35 and 42.

In accordance with the invention, the sleeve-shaped shutter assembly 52 is mounted for rotation within recess 41 such that apertures 60 and 61 may be simultaneously brought into non-registration positions with respect to apertures 46 and 42 whereby light passage through the respective right-angle passageways is prevented. Referring to FIG. 7b, this is accomplished by rotation of the shutter assembly 52 through an angle of approximately 45°, thereby displacing apertures 60 and 61 from the in-registration positions illustrated in FIG. 7a.

To facilitate rotation of shutter sleeve 52 the upper end of the sleeve is preferably provided with a flange portion 62 of increased diameter providing a horizontal support surface 63 which bears against the top surface of test cell module 33. The generally cylindrical flange portion 62 is dimensioned to provide an interior recess 63 which provides a snug friction-fit with the removable cuvette cap 56.

To provide the operator with a convenient means for rotating the sleeve-shaped shutter assembly 52, the assembly includes an annular collar 64 fitted over the exterior surface of flange portion 62 and rotatably locked thereto by means of a set screw 65 or other appropriate means. An elongated radially-projecting rod-shaped handle 66 is threaded into an appropriately dimensioned bore 67 on the outer surface of collar 64 to assist the operator in rotating the shutter assembly and to provide a readily ascertainable indication of shutter position.

The angle of rotation of the shutter assembly is preferably limited by means of a stationary upwardly-projecting guide pin 70 on the top surface of the test cell module and a cooperating downwardly-facing arcuate slot 71 in collar 64. As best seen in FIG. 3, the effect of the guide pin and slot is to prevent rotation of the collar, and hence the shutter assembly, beyond a fixed arc of approximately 45°. Furthermore, the provision of these elements assures that the shutter assembly will be properly aligned when inserted in recess 41, since the guide pin 70 would prevent the shutter assembly from being fully seated if the alignment were not correct. In this way, accurate positioning of apertures 60 and 61 with respect to apertures 46 and 42 is assured. To provide for convenient and positive positioning of the shutter assembly, it is preferable that a controlled degree of friction exists between the shutter assembly and the housing of test cell module 33. In the present embodiment this friction is provided by means of an elongated set screw 73 formed of Delrin or similar plastic material which is brought to bear against the exterior surface of the sleeve-shaped shutter. To this end the set screw is received within a threaded aperture 74 which extends through the side of housing 40 in generally perpendicular radial alignment with aperture 41. The desired degree of friction can be readily set by the operator by adjustment of set screw 73 from the exterior of the test cell module.

Referring to FIG. 8, in operation liquid material to be tested is placed within cuvette 51 and an initial dark current correction reading is made with the shutter positioned as shown in FIG. 7b. Then, shutter assembly is positioned as shown in FIG. 7a, allowing the liquid sample within cuvette 51 to be exposed to excitation light from lamp 27 through filter 48, aperture 46 and aperture 60. Light emitted as a result of fluorescence in the sample passes through apertures 61 and 42 to photomultiplier tube 25 to provide continuous fluorescence emission readings. When subsequently changing samples, the shutter assembly is again positioned as shown in FIG. 7b, thereby simultaneously interrupting the light paths to and from the sample and allowing the cuvette to be removed and replaced with another cuvette without danger of exposing the photomultiplier tube 25 to ambient or reflected light. It will be appreciated that the same procedure applies to continuous-flow systems, and that adjustments to such systems may be readily made when the shutter assembly is positioned as shown in FIG. 7b with the same protection to photomultiplier tube 25.

By reason of the compact arrangement of the excitation lamp and photomultiplier tube in the fluorometric analyzer head assembly 30, the optical paths between the active elements are relatively short, and therefore the instrument is capable of high sensitivity. Furthermore, because of the compact arrangement provision may be made for circulating temperature-controlled liquid within the head assembly to maintain the assembly at a constant temperature over long periods of time, thereby making the instrument very stable in operation. The shutter assembly of the present invention, because of its compact and simple construction, can be readily incorporated in the head assembly without detriment to either the high sensitivity or high stability attributes of the head assembly.

The shutter assembly of the invention can be utilized in conjunction with other forms of fluorometric analyzers, such as the fluorometric analyzer 80 shown in FIG. 9. This instrument, like the previously described fluorometric analyzer 20, includes an output meter 81 and a plurality of operator-adjustable controls 82. However, in this analyzer, the analyzer head assembly is incorporated within the instrument housing. The excitation lamp (not shown) is accessible through a removable cap 83, and access doors 84 and 85 facilitate operator access to the flow cell of the internal head assembly.

Referring to FIGS. 10-13, analyzer 80 includes a removable test cell module 90 of generally square cross-section which is received within a correspondingly dimensioned aperture in an internal analyzer head assembly (not shown). Basically, the housing 91 of this module includes a bore-shaped aperture 92 in which three slot-shaped apertures 93-95 (FIG. 12) are provided to establish light communication with a liquid sample 96. A generally elongated cylindrical sleeve-shaped shutter assembly 100 is slidable received within aperture 92 and arranged for free rotation with respect to housing 91. Three apertures 101-103 are arranged to provide light communication with the sample to apertures 93-95 when the sleeve-shaped shutter is positioned as shown in FIG. 12. As in the previously described embodiment, upon rotation of the sleeve assembly these apertures are simultaneously displaced from the in-registration positions shown to out-of-registration positions whereby the passage of light through the three passageways is simultaneously inhibited.

To facilitate user positioning of the shutter assembly, an annular collar 104 is fitted over the upper end of shutter 100 and rotatably locked thereto by means of a set screw 105 or other appropriate fastening means. A removable cap 99 is fitted over the exposed end of the collar to cover the cuvette. The first or upper portion 106 of the sleeve-shaped shutter assembly corresponds in diameter to the outside diameter of the cuvette to provide a positive sliding engagement with the cuvette, and a second or bottom portion 107 of reduced diameter forms an annular shoulder 108 on which the cuvette rests. As in the previously described embodiment, cuvette 109 can be replaced with a continuous-flow cell by removal of cap 106 and installation of tubing connecting with an associated flow system.

Referring to FIG. 13, a guide pin 111 formed at the end of a first set screw 112 coacts with a complimentarily positioned arcuate channel 113 on the sleeve-shaped shutter to limit the movement of the shutter. To remove the shutter assembly, it is merely necessary to turn set screw 112 in the direction of disengagement with housing 91 until guide pin 111 is clear of channel 113, at which time the shutter assembly can be pulled upwardly clear of recess 92.

To obtain a degree of frictional engagement between shutter assembly 100 and base 91 a second set screw 114 formed of Delrin or other suitable plastic material is threaded into a second aperture 115 so as to bear against the side wall of the shutter assembly. By adjusting set screw 114 the operator can readily set a desired degree of frictional engagement. As in the previously described embodiment, the collar assembly 104 may be provided with a radially-projecting handle 116 to assist the operator in positioning the shutter assembly.

While particular embodiments of the invention have been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

I claim:

1. A head assembly for a fluorometric analyzer for measuring fluorescence in a liquid sample element contained within a test cell, wherein the analyzer includes,
   an excitation lamp element for applying radiation to the sample, and
   a photodetector element for detecting light produced as a result of fluorescence in the sample;
   said head assembly comprising, in combination:
   a housing defining a bore-shaped chamber, and further defining a first optical passageway between the excitation lamp element and the test cell, and a second optical passageway between the test cell and the photodetector element, said optical passageways being arranged at generally right angles to each other and to the axis of the bore-shaped chamber;
   shutter means comprising a cylindrical sleeve member slidably received within said bore-shaped chamber for simultaneously controlling the passage of light through said first and second optical passageways, said sleeve being mounted for rotation about the axis of said bore-shaped chamber between first and second positions and including a central recess for slidably receiving the test cell, said test cell rotating about said axis with rotation of said sleeve; and
   said sleeve further including first and second apertures arranged for alignment with said first and second optical passageways and said sample-receiving recess for establishing light communication between the excitation lamp element, the sample element, and the photodetector element when said sleeve is in said first position, and arranged for non-alignment with said first and second optical passageways for blocking light communication between said elements when said sleeve is in said second position.

2. A fluorometric analyzer head assembly as defined in claim 3, wherein said first and second apertures substantially correspond to the width of said first and second optical passageways, respectively.

3. A fluorometric analyzer head assembly as defined in claim 1 including friction means comprising a set screw threadingly engaged in said housing for bearing against said sleeve to provide a desired degree of rotational friction between said sleeve and said housing.

4. A fluorometric analyzer head assembly as defined in claim 1 including rotation limiting means for limiting rotation of said sleeve member between said first and second positions.

5. A fluorometric analyzer head assembly as defined in claim 4 wherein said rotation limiting means comprise a projecting pin element and coacting slot element, one of said elements being disposed on said sleeve member, and the other of said elements being disposed on said housing.

6. A fluorometric analyzer head assembly as defined in claim 4 wherein the rotation of said sleeve member is limited to an arc less than 90 degrees.

7. A fluorometric analyzer head assembly as defined in claim 1 wherein the test cell is generally cylindrical in form and said central recess is bore-shaped and dimensioned to slidably receive the test cell.

* * * * *